United States Patent [19]

Pelosi, Jr. et al.

[11] 4,424,367
[45] Jan. 3, 1984

[54] 5-(4-AMINOPHENYL)-2-(THIOPHENECARBOXIMIDAMIDE HYDROCHLORIDE HEMIHYDRATE

[75] Inventors: Stanford S. Pelosi, Jr.; Chia-Nien Yu; Ronald E. White; George C. Wright, all of Norwich, N.Y.

[73] Assignee: Norwich Eaton Pharmaceuticals, Inc., Norwich, N.Y.

[21] Appl. No.: 409,652

[22] Filed: Aug. 19, 1982

[51] Int. Cl.³ .................. C07D 333/48; A61K 31/38
[52] U.S. Cl. ...................................... 549/74; 424/275
[58] Field of Search ........................... 549/74; 424/275

[56] References Cited

U.S. PATENT DOCUMENTS

| | | | |
|---|---|---|---|
| 2,492,632 | 12/1949 | Hartough | 549/74 |
| 3,206,468 | 9/1965 | Grenda | 549/74 |
| 3,299,081 | 1/1967 | Sletzinger et al. | 549/74 |
| 3,313,852 | 4/1967 | Paehter et al. | 549/74 |
| 3,325,506 | 6/1967 | Jones et al. | 549/74 |
| 3,441,607 | 4/1969 | Bell | 549/74 |

Primary Examiner—Alan Siegel
Attorney, Agent, or Firm—Anthony J. Franze

[57] ABSTRACT 5-(4-Aminophenyl)-2-thiophenecarboximidamide hydrochloride hemihydrate is useful as an antidepressant agent.

1 Claim, No Drawings

5-(4-AMINOPHENYL)-2-THIOPHENECARBOXIMIDAMIDE HYDROCHLORIDE HEMIHYDRATE

This invention relates to the compound 5-(4-aminophenyl)-2-thiophenecarboximidamide hydrochloride hemihydrate of the formula:

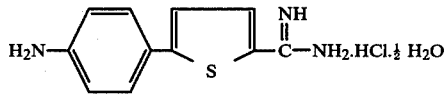

The compound of this invention is useful as an antidepressant agent. Its useful antidepressant activity is exhibited in warm-blooded animals under the standard ptosis-anti-tetrabenazine test. Thus, when administered perorally in suspension or aqueous solution in a dose of 50. mg/kg to mice shortly prior to intraperitoneal administration of from 1–10 mg/kg of tetrabenazine, ptosis induced by tetrabenazine is curtailed to the extent of 67.%.

This compound is preferably prepared in accordance with the following example:

A mixture of 4-nitroaniline (119 g, 0.86 mole), $H_2O$ (170 ml), and concentrated HCl (375 ml) was diazotized by dropwise addition of a solution of $NaNo_2$ (60 g) in $H_2O$ (170 ml), keeping the temperature below 10° with an ice bath. The mixture was stirred for ½ hr and 2-thiophenecarboxaldehyde (100 g, 0.86 mole) was added, followed by a solution of $CuCl_2$ (17 g) in $H_2O$ (40 ml). The mixture was stirred at ambient temperature for 48 hr, ether (600 ml) was added, and the product was collected by filtration. The product was recrystallized from ethanol, yield: 18 g (9%).

A solution of hydroxylamine hydrochloride (5.4 g, 0.078 mole) in $H_2O$ (15 ml) was added to a mixture of 5-(4-nitrophenyl)-2-thiophenecarboxaldehyde (18 g, 0.077 mole) in ethanol (160 ml). The mixture was heated to reflux, the heat was removed, and the mixture was stirred for one hour. The mixture was cooled overnight and the product was collected by filtration, yield: 10 g (53%).

A mixture of 5-(4-nitrophenyl)-2-thiophenecarboxaldehyde oxime (10 g, 0.04 mole) and acetic anhydride (130 ml) was refluxed for 2½ hr, cooled, and poured gradually in $H_2O$ (250 ml). The mixture was stirred for 4 hr and the product was collected by filtration, yield: 8.5 g (91%).

Dry HCl was passed into a mixture of 5-(4-nitrophenyl)-2-thiophenenitrile (8.5 g, 0.027 mole) in absolute alcohol (100 ml) with stirring at 10–15° for 1½ hr. The ice bath was removed, the mixture was stirred for 1½ hr and the product was collected by filtration, yield: 7 g (83%).

A mixture of ethyl 5-(4-nitrophenyl)-2-thiophenecarboximidate hydrochloride (7.0 g, 0.022 mole), $NH_4OAc$ (30 g), and ethanol (200 ml) was refluxed for 7 hr, stored overnight at room temperature and the product was collected by filtration. The product was extracted with dilute HCl (1200 ml), filtered, and the filtrate was adjusted to pH 10 with solid $K_2CO_3$. The product was collected by filtration and air dried, yield: 2 g (37%). The product was combined with 2.7 g of 5-(4-nitrophenyl)-2-thiophenecarboximidamide from a previous reaction and stirred for 45 min in ethanol/HCl (75 ml). The mixture was cooled and the product was collected by filtration, yield: 4 g (74%).

A mixture of 5-(4-nitrophenyl)-2-thiophenecarboximidamide (4 g, 0.014 mole), ethanol (150 ml), and 5% Pd/C-50% $H_2O$ (0.8 g) was subjected to hydrogenation at room temperature for 24 hr, using 42.5 psia $H_2$ (theory: 42.0 psia). Methanol (400 ml) was added and the reaction mixture was heated. The mixture was filtered hot to remove the catalyst. The filtrate was reduced in volume to 200 ml under reduced pressure, cooled, and the product was collected by filtration, yield: 2 g (54%). A sample was recrystallized from methanol, m.p. 293°–300° dec.

Anal. Calcd. for $C_{11}H_{11}N_3S \cdot \frac{1}{2}H_2O$: C, 50.28; H, 4.99; N, 15.99; $H_2O$, 3.43. Found: C, 50.22; H, 4.61; N, 16.11; $H_2O$, 1.19.

What is claimed is:
1. The compound 5-(4-aminophenyl)-2-thiophenecarboximidamide hyrocholoride hemihydrate.